United States Patent
De Guise et al.

(10) Patent No.: US 7,481,780 B2
(45) Date of Patent: Jan. 27, 2009

(54) METHOD OF CALIBRATION FOR THE REPRESENTATION OF KNEE KINEMATICS AND HARNESS FOR USE THEREWITH

(75) Inventors: Jacques A. De Guise, Montréal (CA); L'Hocine Yahia, Pointe-Claire (CA); Nicolas Duval, Montréal (CA); Nicola Hagemeister, Montréal (CA); Gérald Parent, Mascouche (CA); Nancy St-Onge, Montréal (CA); Annick Koller, Montréal (CA); Borislav Anguelov, Montréal (CA); Ismail El Maach, Ottawa (CA)

(73) Assignees: Ecole de Technologie Supérieure, Montréal (CA); Centre Hospitalier de l'Université de Montréal (CHUM), Montréal (CA); Polyvalor, Société en Commandite, Montréal (CA)

( * ) Notice: Subject to any disclaimer, the term of this patent is extended or adjusted under 35 U.S.C. 154(b) by 219 days.

(21) Appl. No.: 10/497,170

(22) PCT Filed: Dec. 11, 2002

(86) PCT No.: PCT/CA02/01916
§ 371 (c)(1),
(2), (4) Date: Feb. 25, 2005

(87) PCT Pub. No.: WO03/053244
PCT Pub. Date: Jul. 3, 2003

(65) Prior Publication Data
US 2005/0143676 A1    Jun. 30, 2005

Related U.S. Application Data
(60) Provisional application No. 60/338,701, filed on Dec. 11, 2001.

(51) Int. Cl.
A61B 5/103 (2006.01)
A61B 5/117 (2006.01)
A61B 17/58 (2006.01)
A61B 17/60 (2006.01)
G06G 7/48 (2006.01)
G06G 7/58 (2006.01)
A61F 5/04 (2006.01)

(52) U.S. Cl. .......... 600/595; 600/587; 600/594; 703/11; 606/102

(58) Field of Classification Search .......... 600/595, 600/587, 594; 703/11; 606/102
See application file for complete search history.

(56) References Cited
U.S. PATENT DOCUMENTS
4,425,713 A * 1/1984 Rotella ............ 33/515
(Continued)

FOREIGN PATENT DOCUMENTS
WO    WO 00/48507    8/2000
WO    WO 01/32080    5/2001

OTHER PUBLICATIONS
Alexander L. Bell et al., A Comparison of the Accuracy of Several Hip Center Location Prediction Methods, *Journal of Biomechanics*, vol. 23, No. 6, pp. 617-621.

Primary Examiner—Max Hindenburg
Assistant Examiner—Jeffrey G Hoekstra
(74) Attorney, Agent, or Firm—Ogilvy Renault LLP (57) ABSTRACT

A method for creating a frame of reference of a leg of a subject for subsequent 3-D kinematic analysis of the leg with non-invasive trackable references secured to the femur and the tibia of the leg. The method comprises the steps of: i) obtaining tibial and femoral axes with respect to the trackable references by tracking points and motions of the leg; ii) registering a known posture of the subject with respect to the trackable references; iii) obtaining a desired posture of the subject with respect to the trackable references as a function of the known posture by tracking a predetermined motion of the leg; and iv) setting a frame of reference to said tibial and femoral axes of the leg in the desired posture of the subject with respect to the trackable references.

3 Claims, 13 Drawing Sheets

U.S. PATENT DOCUMENTS

| | | | |
|---|---|---|---|
| 4,631,676 A * | 12/1986 | Pugh | 600/595 |
| 4,649,934 A * | 3/1987 | Fraser et al. | 600/595 |
| 4,730,625 A * | 3/1988 | Fraser et al. | 600/594 |
| 4,804,000 A * | 2/1989 | Lamb et al. | 600/587 |
| 5,007,912 A * | 4/1991 | Albrektsson et al. | 606/87 |
| 5,611,353 A * | 3/1997 | Dance et al. | 600/595 |
| 5,682,886 A * | 11/1997 | Delp et al. | 600/407 |
| 6,692,447 B1 * | 2/2004 | Picard | 600/587 |
| 6,890,312 B1 * | 5/2005 | Priester et al. | 600/595 |
| 7,209,776 B2 | 4/2007 | Leitner | |
| 2004/0230199 A1 * | 11/2004 | Jansen et al. | 606/91 |
| 2006/0282023 A1 | 12/2006 | Leitner | |

* cited by examiner

METHOD OF CALIBRATION FOR THE REPRESENTATION OF KNEE KINEMATICS AND HARNESS FOR USE THEREWITH

CROSS-REFERENCE TO RELATED APPLICATIONS

This application is a national entry of International Patent Application No. PCT/CA02/01916, filed on Dec. 11, 2002, and claims priority on U.S. Provisional Patent Application No. 60/338,701, filed on Dec. 11, 2001.

TECHNICAL FIELD

The present invention generally relates to three-dimensional (3-D) kinematic representation of the knee and, more particularly, to a calibration method and a reference system therefor.

BACKGROUND ART

The knee joint is one of the most complicated joints in the human body. The tibial and femoral motions involve various translations and rotations, due to leg movements in abduction/adduction, internal/external rotations, and flexion/extension.

When injury occurs to the knee or when diseases as osteoarthrosis set in, reliable diagnosis and treatment evaluation are necessary. For that, functional evaluation of the knee in a three-dimensional manner is essential.

Sophisticated methods exist to measure the functional state of the knee in a dynamic manner. However, these methods are not precise enough to allow the measurement of small angles such as abduction/adduction, and internal/external tibial rotation. Small displacements are tainted by the noise caused by soft tissue movements relative to the bones.

Some have dealt with the problem of skin movement by inserting cortical pins into the bones. With this method, they were able to precisely measure angles in the frontal and transverse planes during gait. However, such methods cannot be widely used in a clinical environment. Some knee braces and harnesses have been developed in order to get 3-D representations of the knee kinematics in a non-invasive manner. For instance, International publication No. WO 01/32080 A1 describes a system for the precise measurement of 3-D knee kinematics.

After a movement has been measured precisely and reliably, it is necessary to represent it in a meaningful way. The knee is not a hinge, and movement about that joint does not occur in a 2D plane. Therefore, it is difficult to represent knee kinematics in a reproducible way.

To improve accuracy and repeatability, most investigators use x-rays to build coordinate systems. This involves radiation for the subject and is not practical because of the need to have access to radiological equipment and to a technician.

SUMMARY OF INVENTION

It is therefore a feature of the present invention to provide a reproducible calibration method for creating a frame of reference of a leg of a subject for subsequent 3-D kinematic representation thereof.

It is a further feature of the present invention to provide a reproducible calibration method for positioning a frame of reference on a leg of a subject at given postures of the subject for subsequent 3-D kinematic representation thereof.

It is still a further feature of the present invention to provide reproducible femoral and tibial axes upon which will be based coordinate systems for 3-D kinematic representation of a leg.

It is still a further feature of the present invention to provide a harness to be used with the reproducible calibration method.

According to the above feature of the present invention, and according to a broad aspect thereof, there is provided a method for creating a frame of reference of a leg of a subject for subsequent 3-D kinematic analysis of the leg with non-invasive trackable references secured to the femur and the tibia of the leg, comprising the steps of i) calculating a femoral head center of the leg with respect to the trackable references; ii) digitizing a tibial reference point on the tibia with respect to the trackable references; iii) obtaining a knee reference point with respect to the trackable references by calculating a knee axis by tracking a flexion displacement of the tibia with respect to the knee and identifying a midpoint of said knee axis; and iv) obtaining a frame of reference with respect to the trackable references by relating the femoral head center of the knee reference point in a femoral axis, and the knee reference point to the tibial reference in a tibial axis; wherein the steps i), ii) and iii) are carried out in any sequence.

According to a further broad aspect of the present invention, there is provided a method for creating a frame of reference of a leg of a subject for subsequent 3-D kinematic analysis of the leg with non-invasive trackable references secured to the femur and the tibia of the leg, comprising the steps of: i) obtaining tibial and femoral axes with respect to the trackable references by tracking points and motions of the leg; ii) registering a known posture of the subject with respect to the trackable references; iii) obtaining a desired posture of the subject with respect to the trackable references as a function of the known posture by tracking a predetermined motion of the leg; and iv) setting a frame of reference to said tibial and femoral axes of the leg in the desired posture of the subject with respect to the trackable references.

According to a still further broad aspect of the present invention, there is provided a harness for attachment about a knee femur of a subject. Said harness is comprised of a rigid and non-flexible frame supporting two resiliently mounted clamping means. The clamping means are urged under pressure outwardly for application against a skin outer surface at predetermined medial and lateral sites relative to a femur. A non-resilient adjustable stabilizing element is connected to said rigid frame and disposed at a predetermined location with respect to said medial clamping means in spaced relationship therewith and adjustable for clamping contact on a skin outer surface and in alignment with the center of a medial condyle of the femur to stabilize said rigid frame about a knee. An attachment means is secured to said harness and has means for securement above the knee, wherein said rigid and non-flexible frame is adapted for being connected to the other side of the clamping means such that the harness may be used on a left or a right knee femur.

BRIEF DESCRIPTION OF DRAWINGS

A preferred embodiment of the present invention will now be described with reference to the accompanying drawings in which.

DESCRIPTION OF PREFERRED EMBODIMENTS

Figure 1:
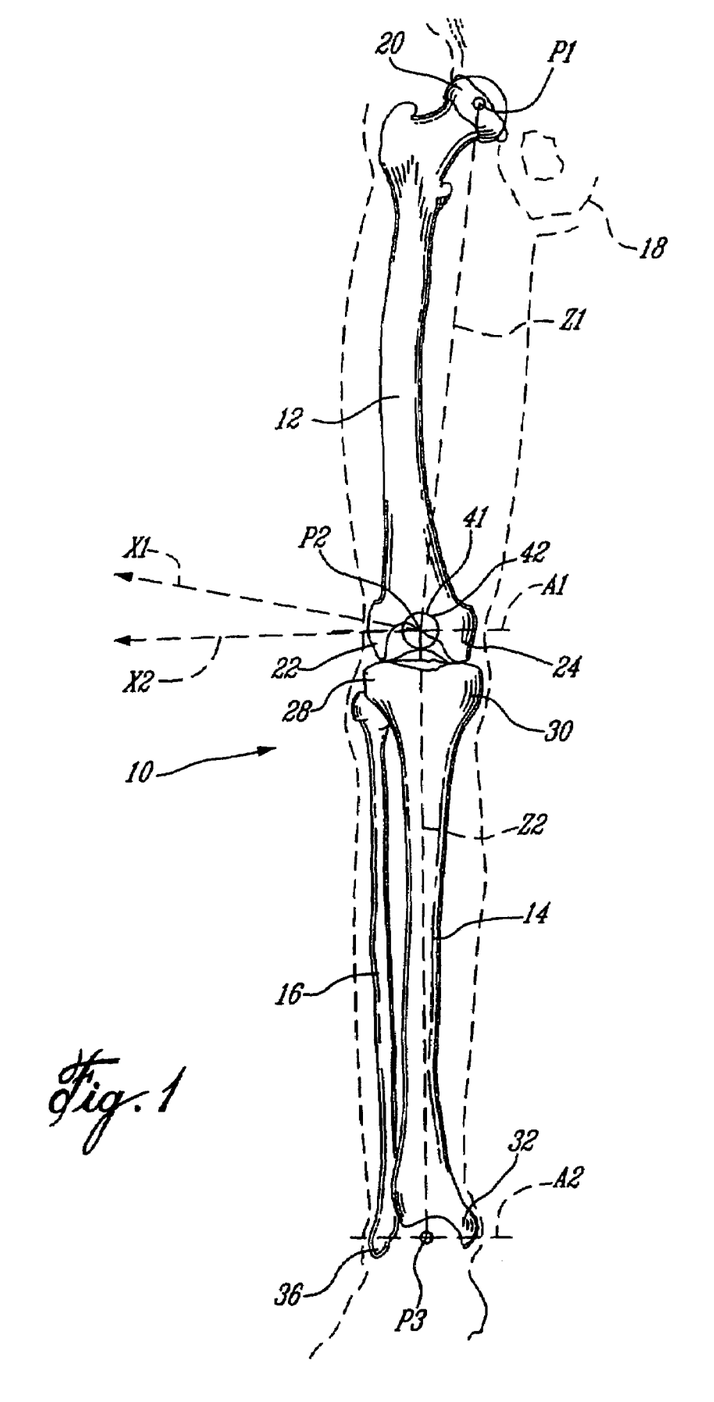
FIG. 1 is a front elevational view of femoral and tibial calibration axes in accordance with the present invention as positioned on bones of a leg.

Referring now to FIG. 1, a right leg of a person is generally shown at 10. For clarity purposes, only the bones involved in the calibration method of the present invention are shown in the right leg 10, namely the femur 12, the tibia 14, the fibula 16 and the pelvis 18. The femur 12 has a femoral head 20 at an upper end thereof, and a lateral condyle 22 and a median condyle 24 at a bottom end thereof. The femoral head 20 is received in the pelvis 18, and the engagement therebetween is equivalent to that of a spherical joint (i.e., three rotational degrees of freedom). The tibia 14 also has a lateral condyle 28 and a median condyle 30 upon which rest the lateral condyle 22 and the median condyle 24 of the femur 12, respectively. The tibia 14 further comprises a median malleolus 32. The fibula 16 has a lateral malleolus 36.

Figure 6A:
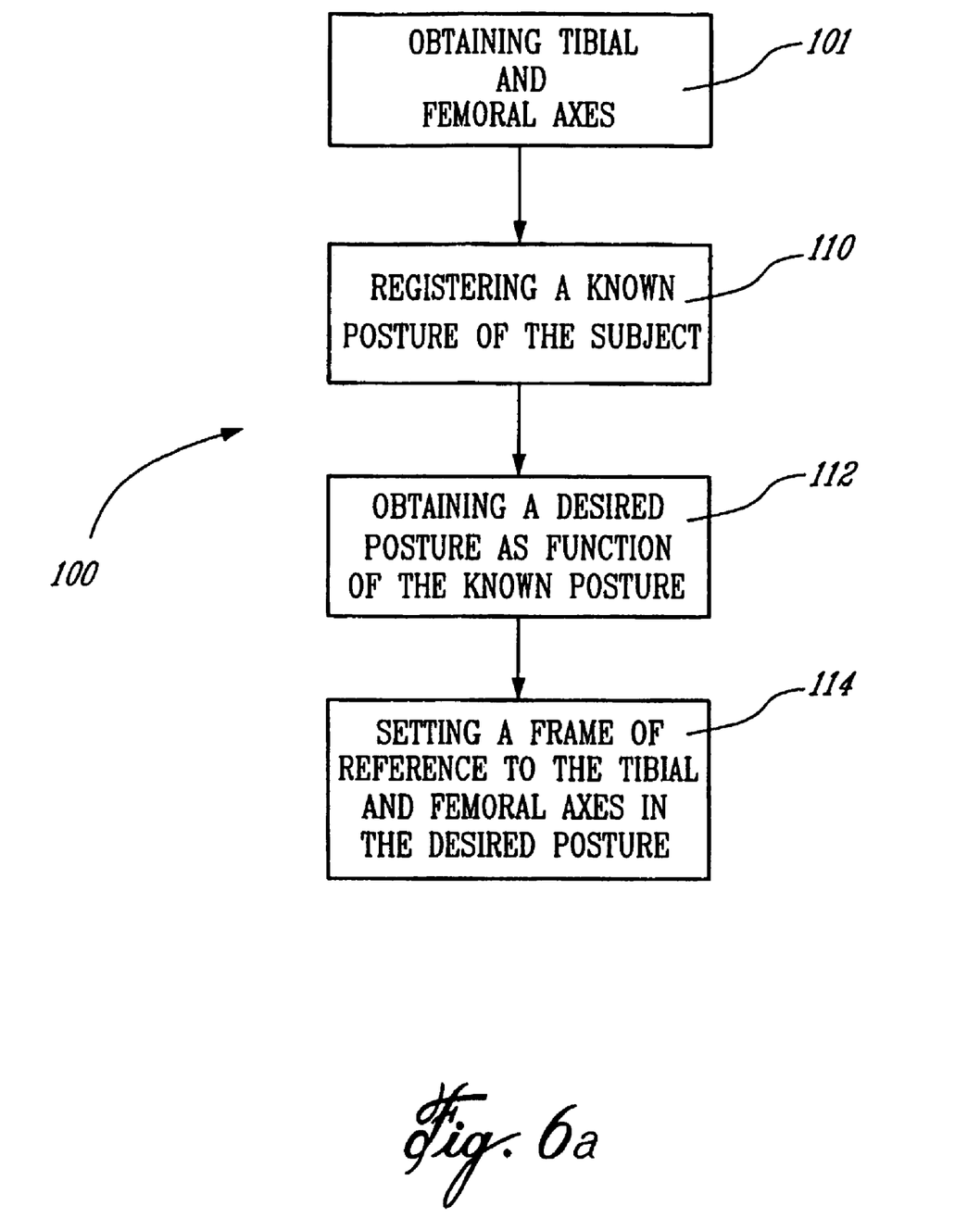
FIG. 6a is a block diagram illustrating the calibration method.

The calibration method of the present invention, illustrated at 100 in FIG. 6a, will enable placement of a frame of reference in the form of a femoral coordinate system on the femur 12 and a tibial coordinate system on the tibia 14, in a reproducible manner from calibration to calibration, such that the frame of reference can be used as a reference during the 3-D kinematic analysis as reference. A femoral axis Z1 of the femoral coordinate system extends from a point P1, at a center of the femoral head 20, to a point P2, at a condyle midpoint of a flexion/extension axis A1, as will be described in further detail hereinafter. A tibial axis Z2 of the tibial coordinate system projects from the point P2 to a point P3, which is at a midpoint between outermost points of the median malleolus 32 of the tibia 14 and the lateral malleolus 36 of the fibula 16.

Figure 2:
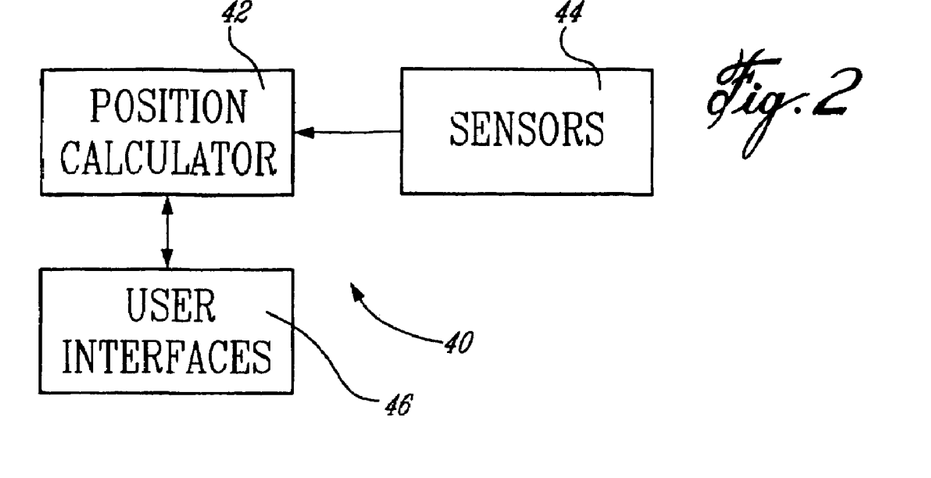
FIG. 2 is a block diagram of a 3-D kinematic representation system in accordance with the present invention.

Referring to FIG. 2, a 3-D kinematic representation system to be used with the calibration method of the present invention is generally shown at 40. The 3-D kinematic representation system 40 typically comprises a position calculator 42, which is a computer having a position calculator software. The position calculator 42 is wired to sensors 44, which detects the position and orientation in a working range thereof of detectable devices. User interfaces 46 are also connected to the position calculator 42 and enable a user to control the position calculator 42 or view the 3-D representation outputted thereby. The user interfaces 46 are typically a monitor, a keyboard and a mouse.

Figure 6B:
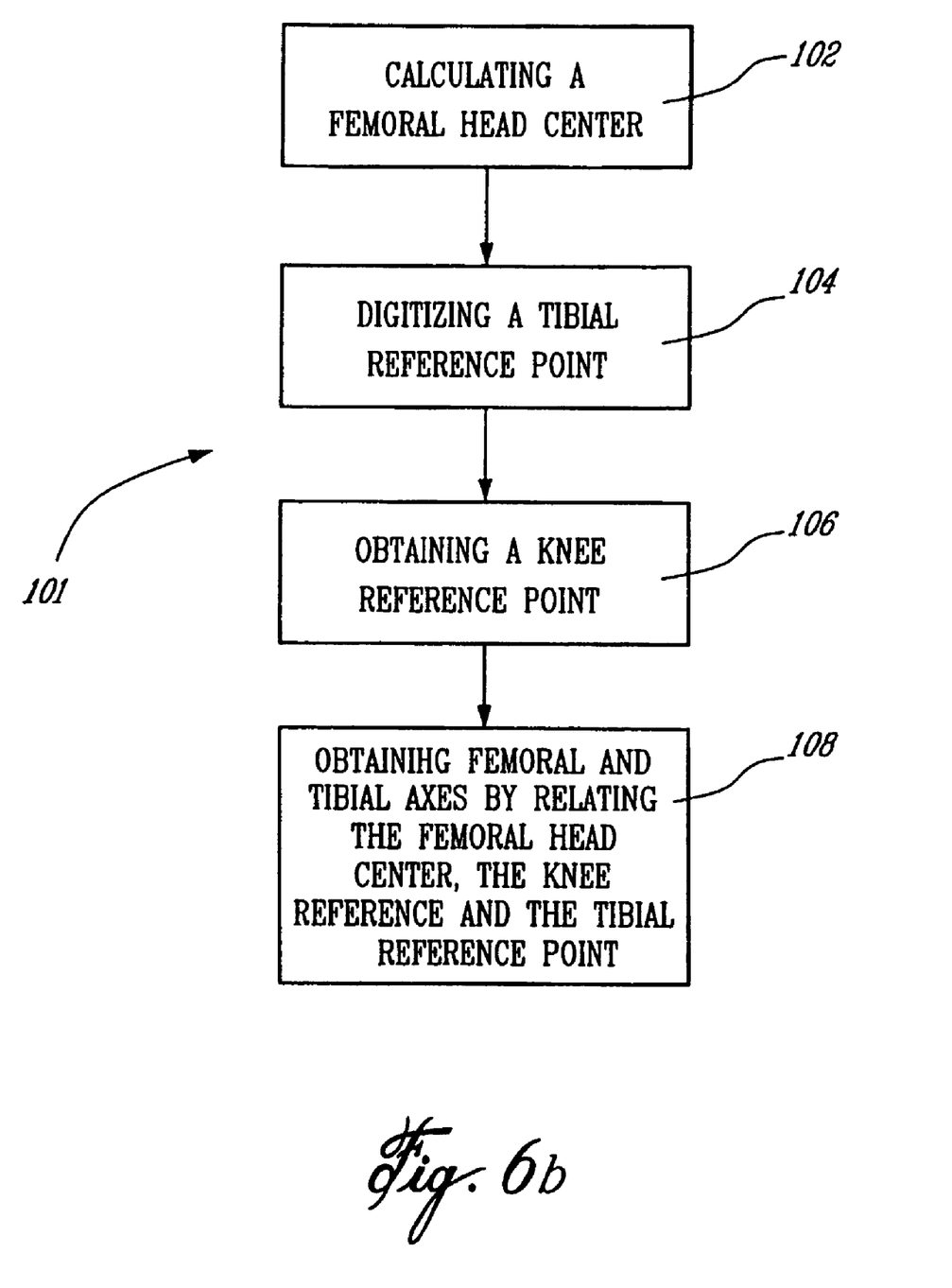
FIG. 6b is a block diagram illustrating a first step of the calibration method.

Referring now to both FIG. 6a and FIG. 6b, a first step 101 of the calibration method 100 is illustrated. Prior to the calibration method 100, a first marker 50 must be immovably secured to the femur 12. The first marker 50 is trackable in space for position and orientation. Therefore, the first marker 50 has at least three points thereof detectable and in a known relation, such that all six degrees of freedom of the first marker 50 are calculable when tracking same. Preferably, the first marker 50 is held against a lower portion of the femur 12, such as the condyle 28 or 30, where only a thin layer of skin tissue separates the first marker 50 from the femur 12. With the fixed relationship between the first marker 50 and the femur 12, the tracking of the first marker 50 ensures that a femoral reference point given by the first marker 50 is in a fixed relation with the femur 12 throughout the calibration and the 3-D kinematic analysis. Therefore, other points may be established on the femur 12 with respect to the femoral reference point so as to be trackable in space through the first marker 50. Various types of first markers 50 may be used, and it is preferable to use clamping devices such as the harness disclosed in International Publication No. WO 01/32080 A1, which minimizes the movement of the first marker 50 with respect to the femur, whereby this movement is negligible. The harness disclosed therein is advantageous, as its construction allows for it to be used on either the right or the left leg by detaching the arch portion thereof and reconnecting it for the change of leg. Also, the harness disclosed in this publication follows the knee closely in its median portion, whereby it does not interfere with the gait of the person so as to have a good representation thereof in the kinematic analysis. This will be described in detail hereinafter.

Similarly, a second marker 52, trackable for position and orientation, must be applied to the tibia 14 so as to remain fixed thereon throughout the calibration to define a tibial reference point at a point of contact between the second marker 52 and the lower leg. Once more, it is preferable to apply the second marker 52 on a position where the skin tissue is thin on the tibia 14, for instance on the shin, thereby ensuring that the tibial reference point remains fixed thereon. The first marker 50 and the second marker 52 are to be used for the 3-D kinematic analysis of the leg, and must be calibrated. The markers 50 and 52 are the trackable references with respect to which the frame of reference will be created.

Figure 3:
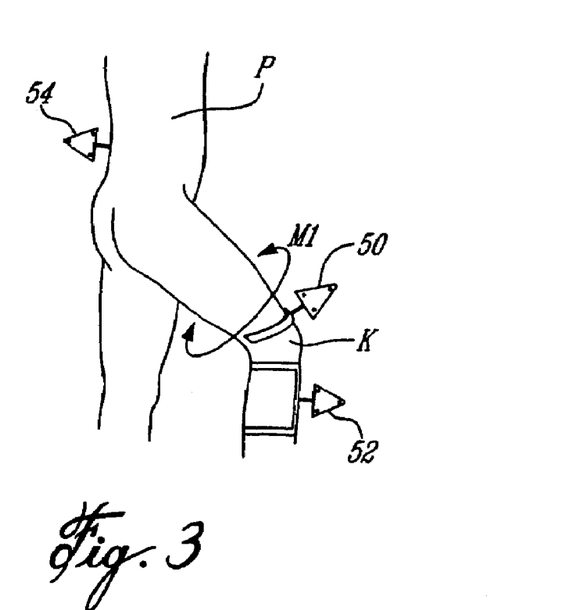
FIG. 3 is a schematic view of a step of a calibration method of the present invention wherein a femoral head center is obtained.

According to the step 101, the femoral axis Z1 and the tibial axis Z2 are obtained. More specifically, referring to FIG. 6b, step 101 is divided into various steps. In step 102, the center P1 of the femoral head 20 is positioned with respect to the femoral trackable reference (i.e., as given by the first marker 50). This is achieved, for instance, by a patient P (i.e., a subject of the kinematic analysis) doing a leg circling movement with his knee K generally defining circles, as shown by arrow M1. Other motions can be performed to obtain the femoral head center. In doing so, the femur 12 rotates as a result of the femoral head 20 being in a spherical joint relationship with the pelvis 18. This motion is tracked by the sensors 44 recording the motions of the first marker 50, thereby enabling the position calculator 42 to calculate the position of the point P1. During the leg circling motion of step 102, the pelvis 18 will move, which will create unwanted displacement of the first marker 50 during the step 102. Therefore, this displacement must be taken into account in calculating the position of the point P1 with respect to the femoral reference point given by the first marker 50. Therefore, as illustrated in FIG. 3, a third movable marker 54 is positioned against the pelvis 18 (preferably on the sacrum, where the skin layer is thin) in order to record the motion of the pelvis 18 while the knee K is doing the circling motion. Therefore, the motion of the pelvis 18 and of the first marker 50 are measured, and the motion of the first marker 50 is calculated with respect to the motion of the pelvis 18. The center of the femoral head P1 is calculated by the position calculator 42. It is pointed out that other methods can be used to position the femoral head center, e.g., using regression equations.

Referring to FIG. 6b, a step 104 follows the step 102 in the calibration method 100. According to the step 104, a tibial reference point is digitized. This is achieved, for instance, by an operator manually finding the outermost points of the lateral malleolus 36 of the fibula 16 and of the median malleolus 32 of the tibia 14. A position for each of the outermost points is digitized with respect to the tibial reference point of the second marker 52 using, for instance, the movable third marker 54. For these purposes, a marker having a reference point at a tip of a pointer thereof is preferably used. Accordingly, once these points are digitized, the position thereof will be known as a function of the position and orientation of the second marker 52. A malleolus axis A2 is then defined between these two outermost points. A point P3 is defined as the median point between the outermost portions of the median malleolus 32 and the lateral malleolus 36, on the malleolus axis A2.

Figure 4:
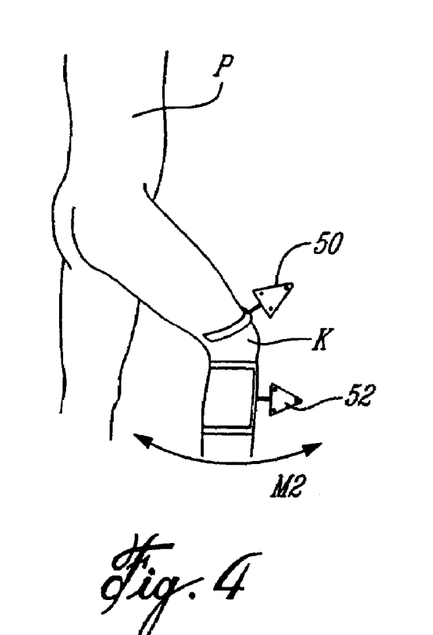
FIG. 4 is a schematic view of a step of the calibration method wherein a knee axis is obtained.

Referring now to both FIG. 4 and FIG. 6b, a step 106 of the calibration method 100 is shown. According to the step 106, a knee reference point is obtained with respect to the reference system. This is achieved by the lower portion of the leg making flexion/extension motions shown at M2. In other words, the lower leg does a kicking motion. In this motion, the knee joint acts as a special hinge which allows the tibia 14 to move with respect to the femur 12 in a three-degrees-of-freedom manner. Therefore, with the first marker 50 on the femoral portion of the leg and the second marker 52 on the tibial portion of the leg, the tracking for position and orientation of these markers will enable calculation by the position calculator 42 of a mean flexion/extension axis A1, about which the lower leg has movements in three degrees of freedom (i.e., two rotations and one translation). Now that the mean flexion/extension axis A1 has been determined, a midpoint P2 thereof is calculated. To do so, the knee thickness at that point must be known. Accordingly, the operator manually finds the outermost points of the knee, i.e., the outermost points of the lateral condyle 22 and of the median condyle 24 of the femur 12 using the movable third marker 54. Once each point is digitized, a thickness approximation of the femur 12 at the knee joint is known. A midpoint P2 is then calculated as half the thickness and positioned (transposed) at the midpoint of the flexion/extension axis A1.

The points P1, P2 and P3, as best shown in FIG. 1, are now all digitized and their positions are calculable as a function of the femoral trackable reference (the first marker 50) and the tibial reference (the second marker 52). Therefore, according to step 108 of FIG. 6b, the points P1 and P2 are related to define the femoral axis Z1, and the points P2 and P3 are related to define the tibial axis Z2, whereby step 101 of the calibration method 100 is completed. These axes are positioned advantageously for representing leg movements, as the points P1, P2 and P3 each represent points about which motion occurs. It is pointed out that the steps 102, 104 and 106 can be performed in any sequence. The femoral axis Z1 and the tibial axis Z2 can be used as a frame of reference to gather some information relating to knee kinematics.

Figure 5A:
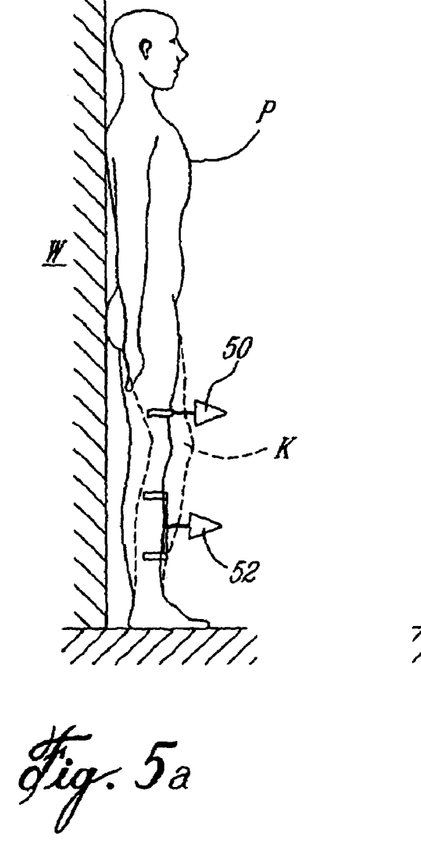
FIG. 5a is a schematic view of a step of the calibration method wherein a desired posture is registered.
Figure 5B:
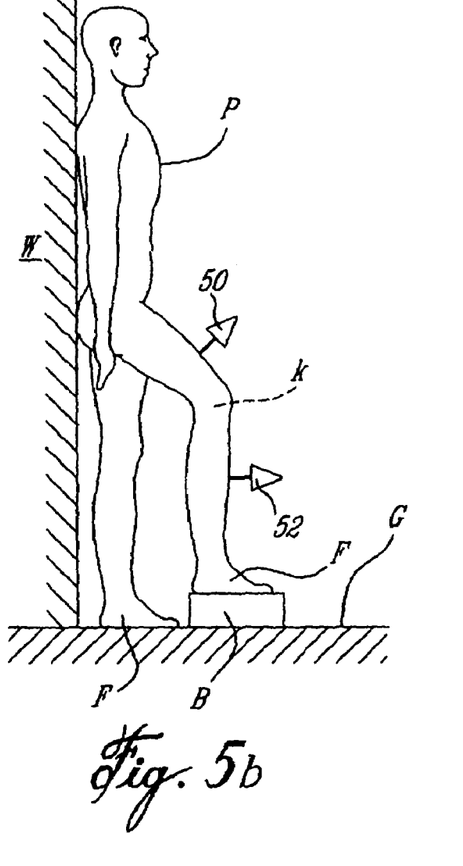
FIG. 5b is a schematic view of the step of FIG. 5a, the calibration method by which an alternative way of registering a desired posture is shown.
Figure 5C:
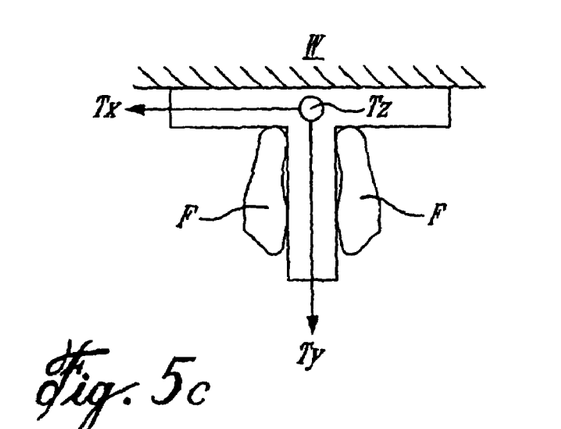
FIG. 5c is a top plan view of a template secured to a wall in which feet of a patient are positioned.

Referring now to FIGS. 5a and 6a, a step 110 follows the step 101 of the calibration method 100. According to the step 110, a known posture of the patient P is registered with respect to the trackable references (markers 50 and 52). One way of achieving the step 110 and registering the known posture is by having the patient P positioned with his back to a wall W. The plane of the wall W is digitized, and this is possible by getting three points thereof digitized with the movable third marker 54, such that the position calculator 42 may calculate the position and orientation of the plane of the wall W, with respect to the trackable references. In order to have a proper positioning of the legs of the patient P, a template T, as illustrated in FIG. 5c for instance, may be provided for the patient P to position his feet F therein, such that the plane of the wall is parallel with the frontal plane of the patient P. A sagittal plane of the subject is defined by the normal of the frontal plane and the vector joining points P1 and P3.

According to step 112, a desired posture is obtained with respect to the trackable references as a function of the known posture. This is achieved by the patient P executing small flexion/extension movements by bending down slightly while keeping his back against the wall (the known posture). In doing so, the full extension of the knee (i.e., at a flexion of 0° between the femoral axis Z1 and the tibial axis Z2) is identified by the position calculator 42. As mentioned above, the full extension is defined at the moment when the angle between the projections on the sagittal plane of Z1 and Z2 is minimal. The desired posture of the knee is then determined at that moment.

Once the desired posture is identified in step 112, step 114 follows. According to step 114, a frame of reference is set to the femoral and tibial axes Z1 and Z2, respectively, as a function of the desired posture of the leg. More specifically, as shown in FIG. 1, the frame of reference has the femoral coordinate system and the tibial coordinate system. The femoral coordinate system originates from point P2 and incorporates the femoral axis Z1. A second femoral axis Y1 is calculated as being perpendicular to the femoral axis Z1 while lying in the sagittal plane of the subject at the desired posture. A third femoral axis X1 is calculated as being perpendicular to the femoral axis Z1 and the second femoral axis Y1.

Similarly, the tibial coordinate system originates from point P2 and incorporates the tibial axis Z2. A second tibial axis Y2 is calculated as being perpendicular to the tibial axis Z2 while lying in the sagittal plane of the subject at the desired posture. A third tibial axis X2 is calculated as being perpendicular to the tibial axis Z2 and the second tibial axis Y2.

An alternative way of performing the steps 110, 112 and 114 is also provided in accordance with the present invention. In this alternative, step 110 is performed by the patient initially positioned with his back to a wall W and his feet F in the template T secured to the wall W, as shown in FIG. 5b. An axis TY of the template T is digitized, perpendicular to the wall W and parallel with the ground G. The template T also permits an axis TX to be digitized, which is parallel to the wall W and to the ground G. An axis TZ is calculated by the position calculator 42 and is perpendicular to the ground G. As mentioned previously, the frontal plane and the sagittal plane can be registered with respect to the wall W, as the subject stands against the wall W. The plane of the wall W is calculated from the TX, TY, TZ coordinate system. Therefore, this known posture of the subject is registered with respect to the trackable references (markers 50 and 52).

According to the step 112, the desired posture must be obtained as a function of the known posture. This is achieved by the position calculator 42 determining a position for the foot F of the referenced leg where it is to be placed with respect to the template T. One way to elevate the foot F consists in using an object B with adjustable height along TZ which can be placed under the foot F at determined distances along TX and TY. In this position, both points P1 and P3 will be in the sagittal plane registered for the known posture in step 110. The position calculator 42 calculates the position of the foot on the object B as a function of the flexion angle between axis Z1 and axis Z2. For instance, an angle of 10° is suitable between the axes. It is noted that the angle is measured from point P2, with axis Z2 projecting upwardly from point P2 to define an angle with axis Z1.

The knee is then oscillated laterally, i.e., in a direction generally parallel to the frontal plane, while the subject remains against the wall W and the foot F in position on the object B. In doing so, the point P2, i.e., the knee reference point, will cross the sagittal plane, at which time points P1, P2 and P3 will all simultaneously be in the sagittal plane. The position calculator 42 records this as the desired posture.

Thereafter, the step 114 is performed in a way similar to that as for the alternative steps 112 and 114. I.e., in the desired postures, femoral and tibial axes X are defined as being simultaneously parallel to the frontal plane and perpendicular to the respective axes Z. As mentioned previously, the femoral axis X1 is positioned to intersect the axis Z1 at the point P2, whereas the tibial axis X2 is positioned to intersect the axis Z2, also at the point P2, and are shown by X1 and X2 in FIG. 1, respectively. Finally, the femoral axis Y1 and the tibial axis Y2 are positioned intersecting the axis Z1 and the axis Z2 at the point P2, respectively, thereby completing the femoral and tibial coordinate systems in an orthonormal fashion, which will serve as frame of reference for a subsequent 3-D kinematic representation in which the markers 50 and 52 will be tracked. Therefore, the calibration method provides reproducible positioning of the femoral coordinate system and the tibial coordinate system.

Referring to FIGS. 7 to 10b, a harness, suitable for the above-described method of calibration, is generally shown at 200. This harness 200 comprises a rigid and non-flexible frame 201 which is formed as a rigid arch. At each end of the frame 201 there is provided a medial rigid support 203 and a lateral rigid support 202. The distance between the ends is fixed or adjustable.

Figures 8A, 8B:
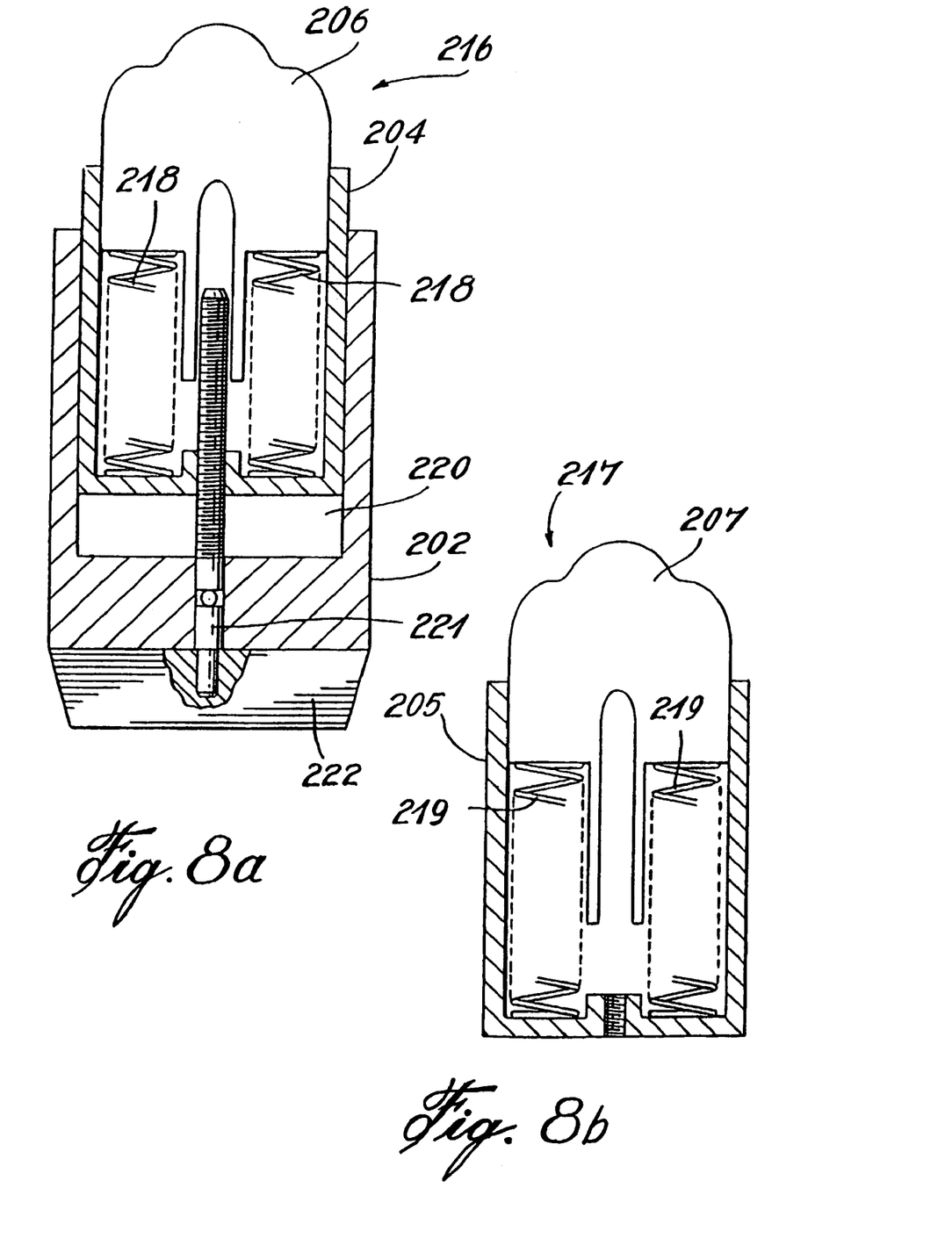
FIGS. 8a and 8b are sectional views of a clamping means of the harness located on a lateral and medial sides of the knee, respectively.

The harness 200 further comprises two resilient clamping means, 216 and 217 as shown in FIGS. 8a and 8b, each of them comprising a rigid housing 204 and 205 in which there are retained two rigid abutment elements 206 and 207, respectively, each having an outer end configured to fit the shape of a condyle. The rigid abutment element 206 will abut against a lateral portion of the knee, whereas the rigid abutment element 207 will abut against a median portion of the knee. Springs 218 and 219, or any other resilient means, apply an outward force on the abutment elements. At least one of the clamping means 216 and 217 could be secured to rigid supports 202 or 203 by adjustable means, e.g., in sliding fit adjustment in a cavity 220 formed in rigid housing 204. This adjustable means is hereinshown as being an adjustment screw 221 having a finger gripping head 222. The springs 218 and 219 are also interchangeable to vary the force of the abutment elements 206 and 207.

Figure 7:
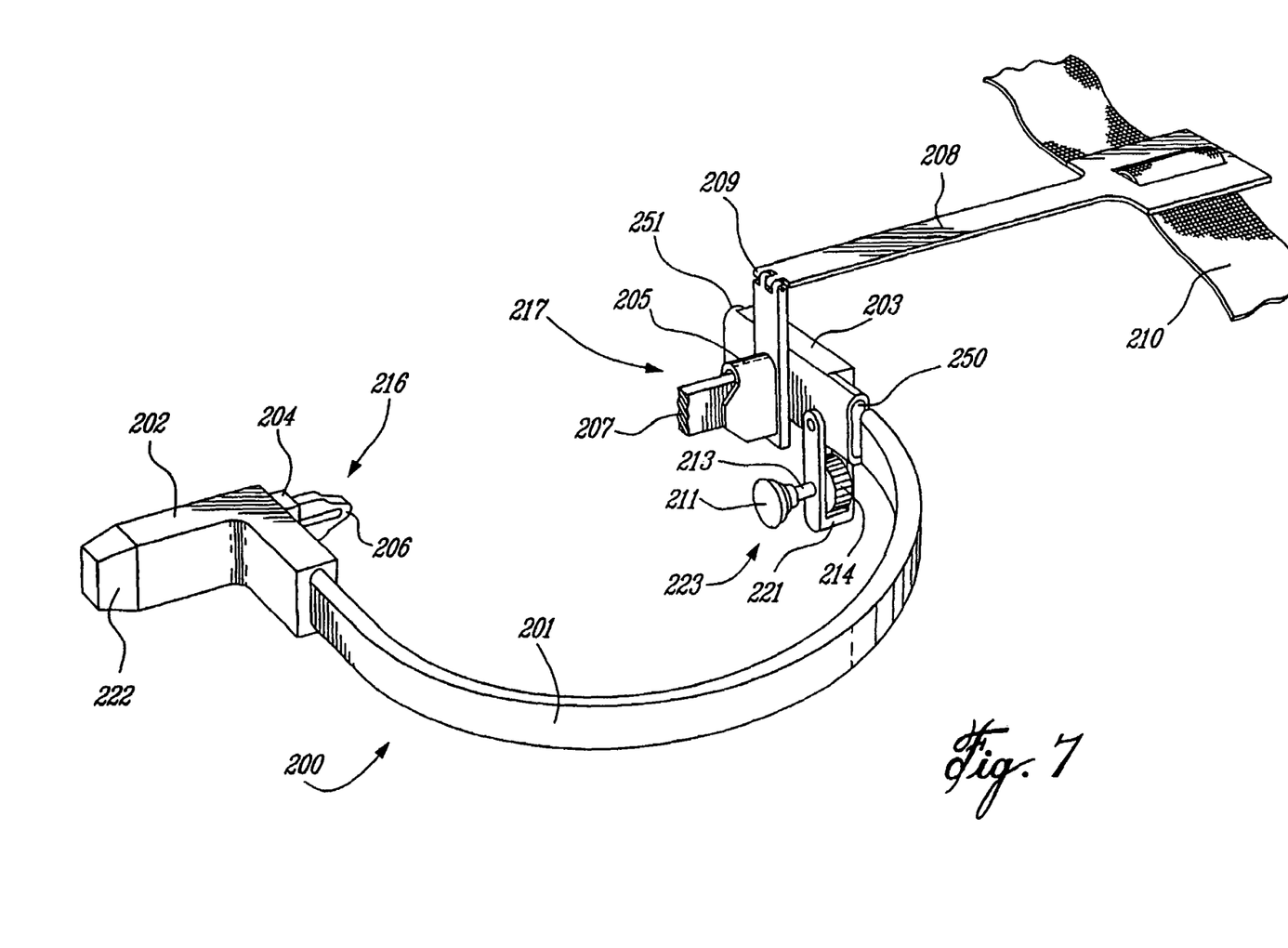
FIG. 7 is a perspective view of a harness constructed in accordance with the present invention.

The harness 200 further comprises a non-resilient adjustable stabilizing element 223 comprising a threaded rod 213 having an abutment pad 211 at an outer end thereof. This stabilizing element 223 is being secured to a support frame 212, which support frame 212, is connected to the rigid frame 203 by adjustable means herein a screw attachment 215. The support frame 212 may thus pivot with respect to the rigid support 203, and then be immobilized by tightening the screw attachment 215. The position of the pad 211 is adjusted by an adjustment wheel 214.

Figure 13:
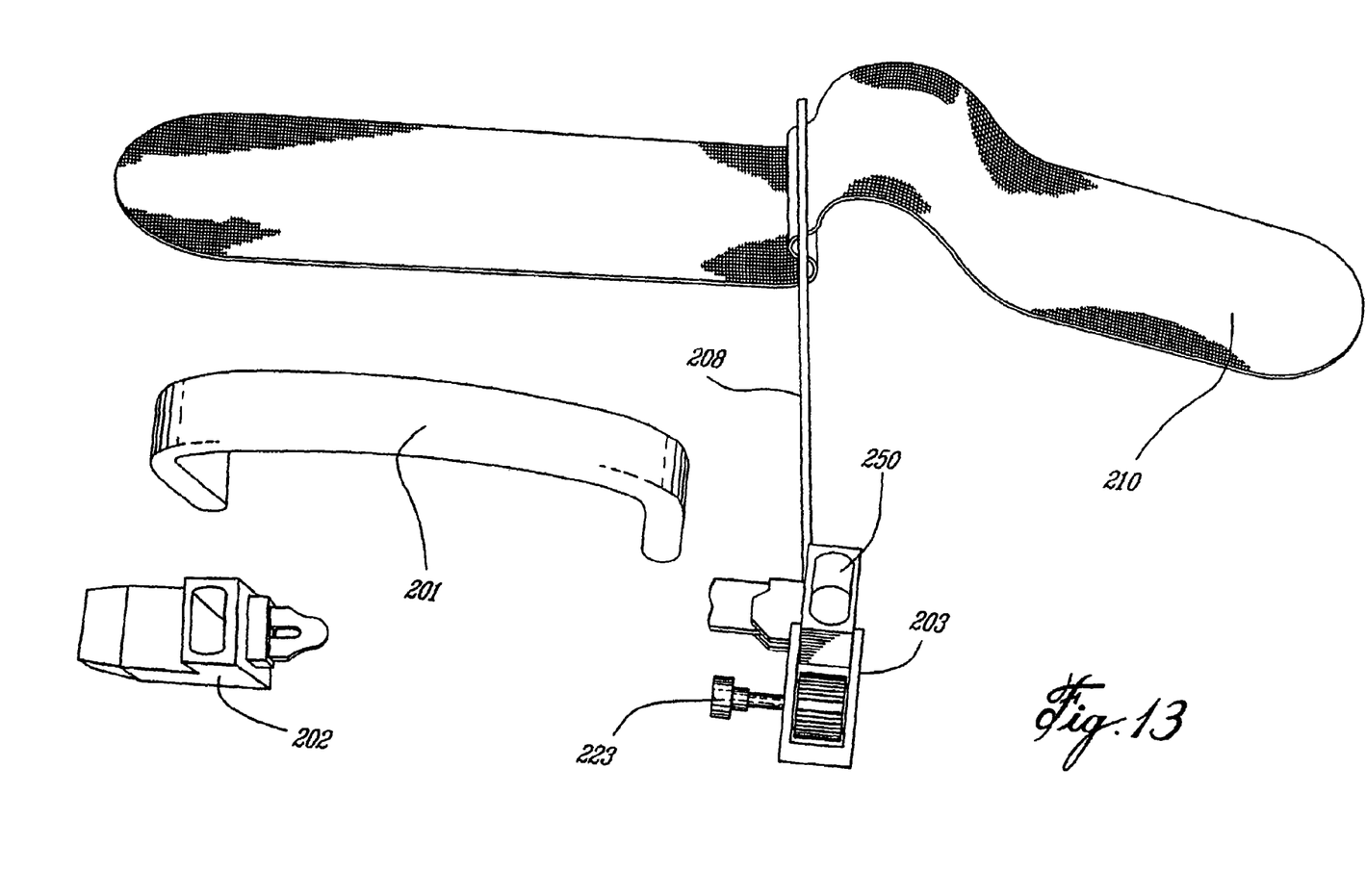
FIG. 13 is a perspective view of the harness as disassembled from FIG. 12.
Figure 15:
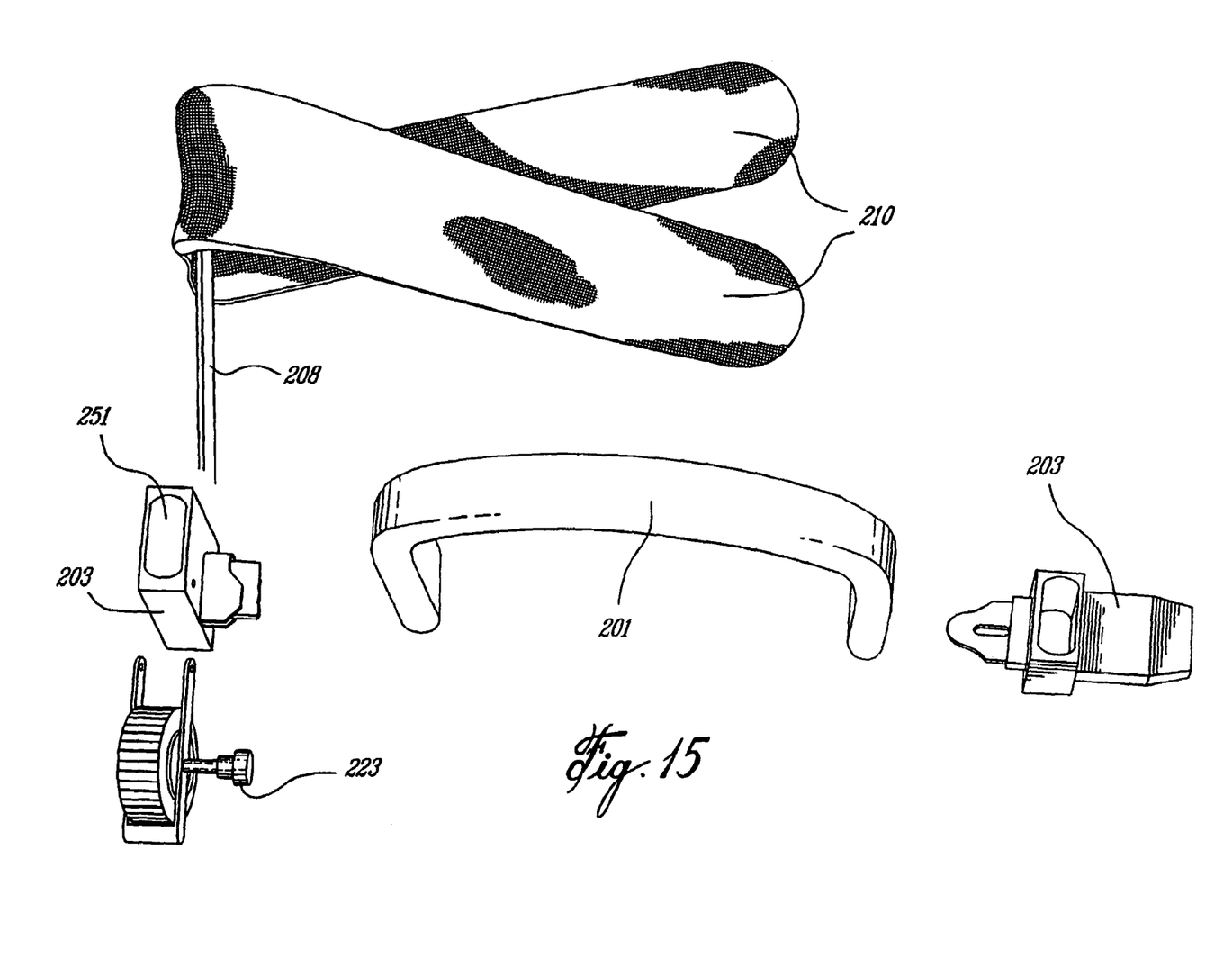
FIG. 15 is a perspective view of the harness as disassembled from FIG. 14.

The medial rigid support 203 defines openings 250 and 251 on opposed surfaces thereof. The openings 250 and 251 are both sized and shaped for receiving a free end of the arch 201. The reception of the arch 201 in either opening 250 or 251 is achieved by an interference fit, a snap-fit engagement, or the like, so as to releasably secure the arch 201 with the medial rigid support. 203. The arch 201 is received in the free opening 250 for the harness 200 to be used on the right leg, and in the opening 251 for the harness 200 to be used on the left leg. The lateral rigid support 202 may, although not required for the harness 200 to be reversible, be detached from the arch 201, as shown in FIGS. 13 and 15.

The harness 200 further comprises an attachment means in the form of a bar 208. This attachment bar 208 is in the form of a long narrow flat plate and could be formed of two sections interconnected by a hinge 209 or by a pivot. The attachment bar 208 could be secured by a Velcro™ strap 210 or by other attachment means above the knee of the wearer.

Figure 9:
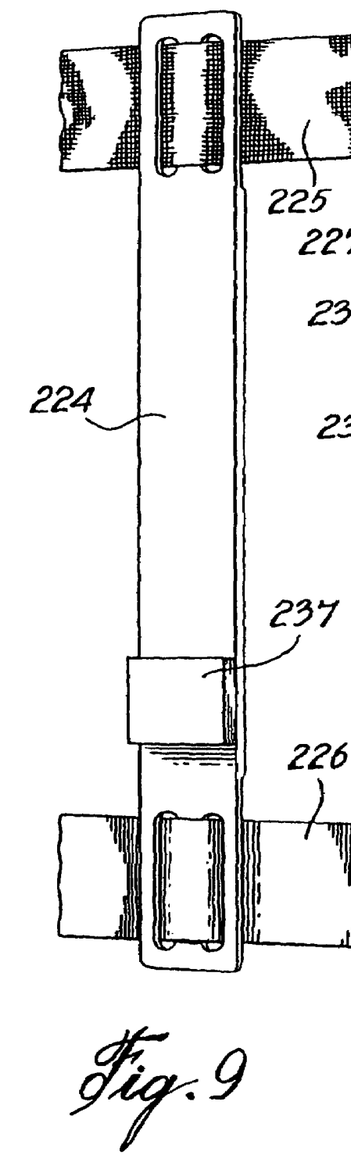
FIG. 9 is a perspective view of a tibial attachment means in accordance with the present invention.

Referring now to FIG. 9, the tibial attachment means is described. This attachment means comprises a tibia attachment bar 224 secured below the knee by means of two adjustable Velcro™ straps 225 and 226, or by other attachment means. This attachment bar 224 is also in the form of a long narrow flat plate.

Figure 10A:
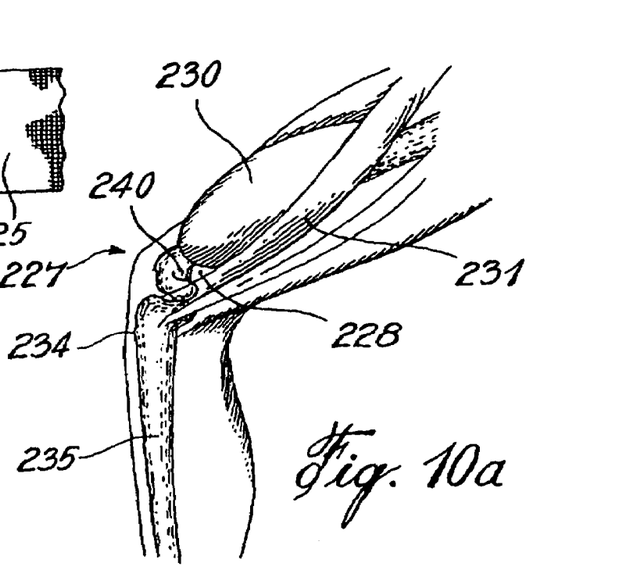
FIGS. 10a and 10b are respectively medial and lateral views of the anatomical structures of the knee, permitting the identification of installation sites of the harness on the knee.
Figure 10B:
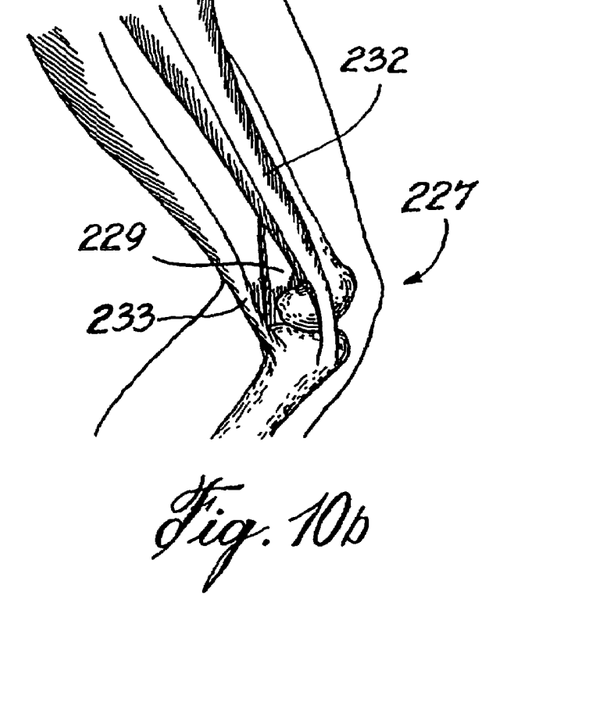
Figure 11:
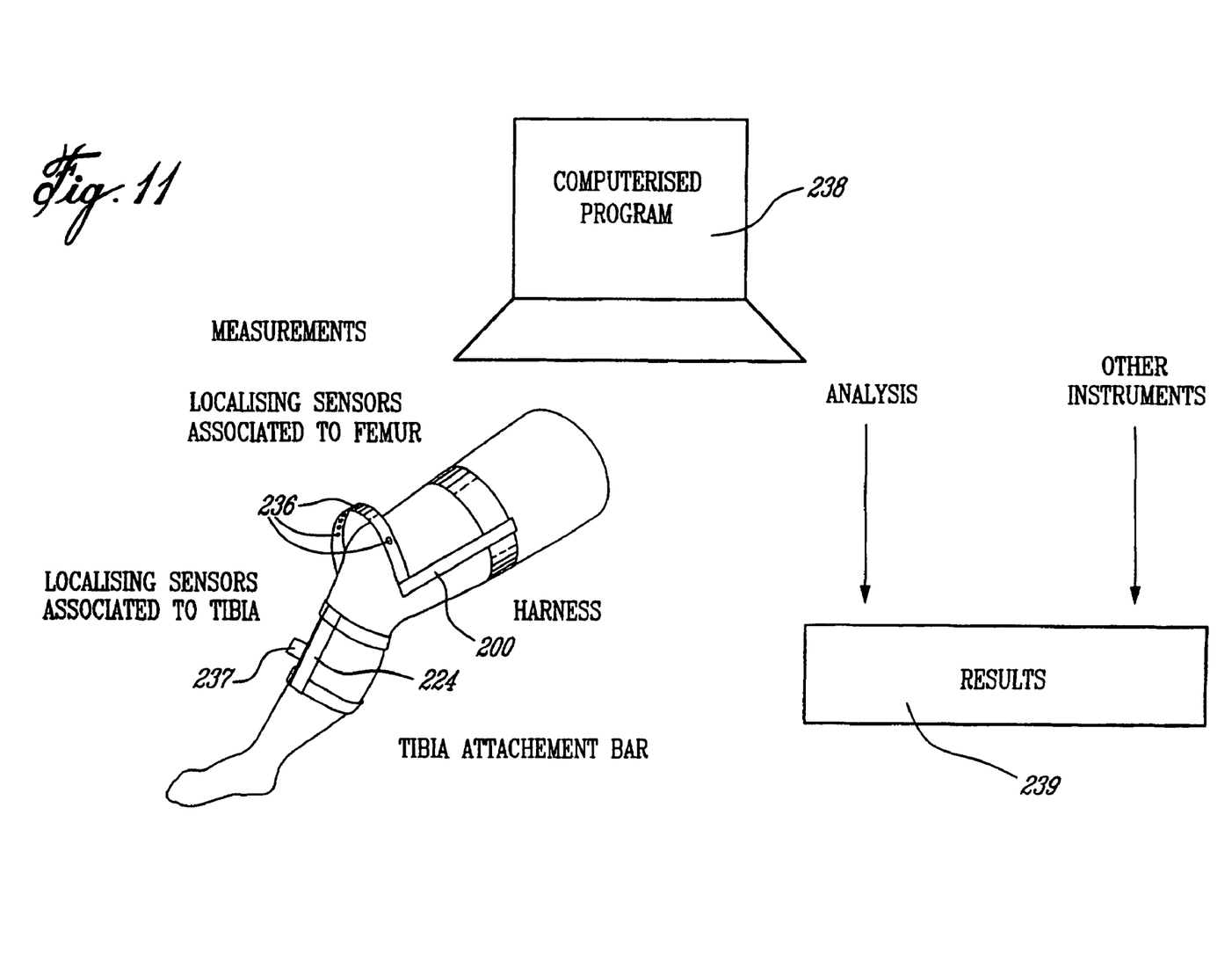
FIG. 11 is a schematic and block diagram representing the system for analysis of the three-dimensional kinematic of the knee.
Figure 12:
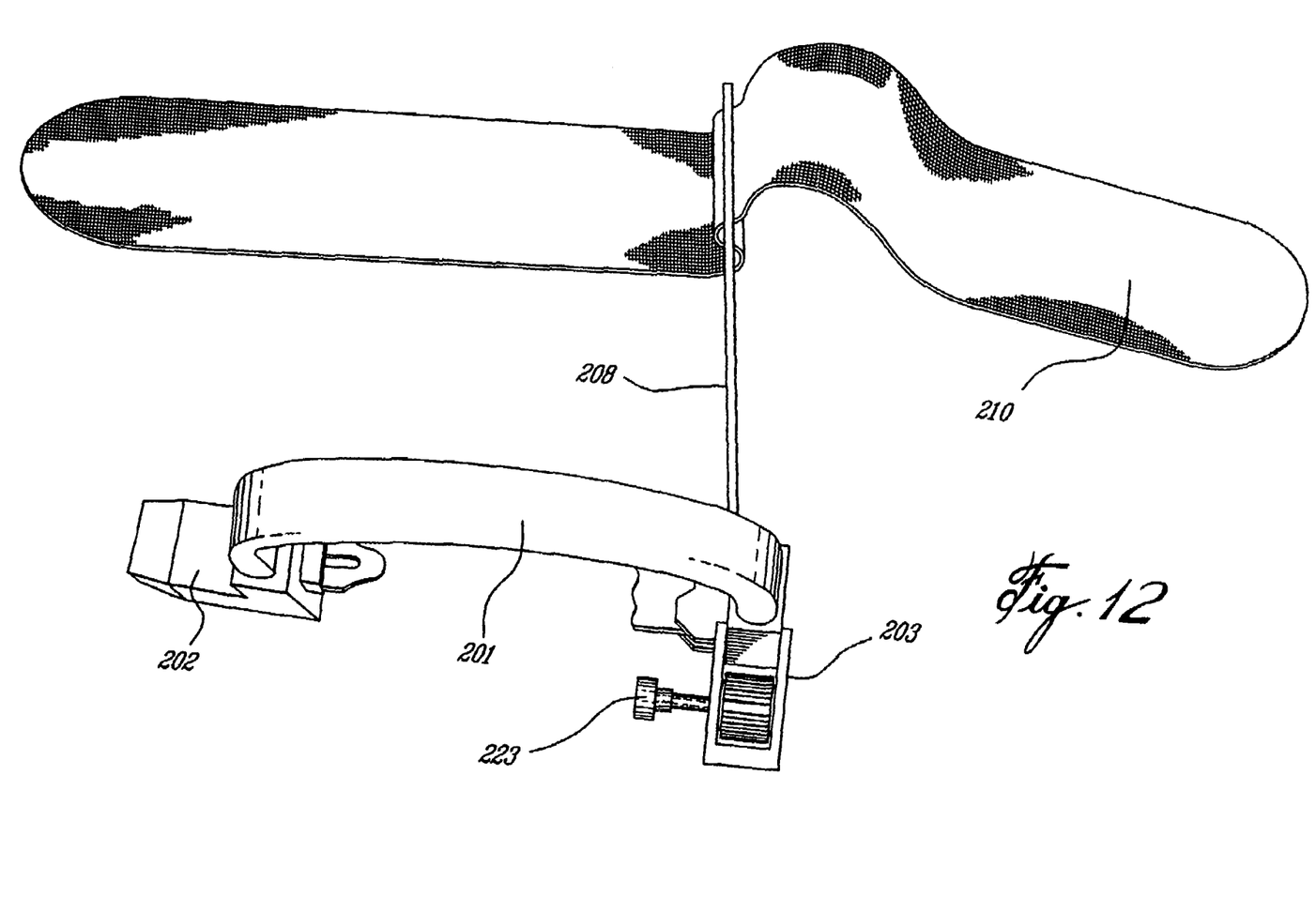
FIG. 12 is a perspective view of the harness as assembled for being used on a right leg.

Referring to FIGS. 7, 10a and 10b, the installation of the harness 200 on knee 227 is described. The harness 200 is installed on the knee 227 by urging the abutment elements 206 and 207 of the clamping means 216 and 217 against the skin at predetermined sites 229 and 228, respectively, on the knee. These predetermined sites are located laterally between the ilio-tibial band 232 and the biceps femoris tendon 233 of the knee and medially between the vastus medialis 230 and the sartorius tendon 231 of the knee. The harness 200 is thereafter secured proximally, rigidly attaching the attachment bar 208 against the medial side of the thigh and securing this attachment bar by means of the Velcro™ strap 210. Without affecting subject's comfort, the harness stability is adjusted by means of the adjustable screw wheel 214. The abutment pad 211 of the stabilizing element 223 is urged against skin in alignment with the center of the medial condyle 228. Therefore, by its configuration, the harness 200 is secured to the upper portion of the leg in a non-invasive manner. Various detectable devices, as will be explained hereinafter, may be secured to the harness 200, such that the harness 200 is tracked for position and orientation in space. As the harness 200 is fixedly secured to the upper leg, whereas the tibial attachment 227 is fixedly secured to the lower leg, the dual tracking for position and orientation gives precise information about relative knee motion.

Referring to FIGS. 9, 10a and 10b, the installation of the tibial attachment on the knee 227 is described. The tibia attachment bar 224 is installed by adjusting its position so that the bar 224 urges on the anterior side of the tibia, below the tuberosity 234 of the tibia 235, securing the tibia attachment bar 224 below this tuberosity by means of the adjustable straps 225 and 226.

Referring to FIG. 1, the method for analyzing the three-dimensional kinematic of a knee will be described. The harness 200 is provided with localizing sensors 236 and the tibial attachment bar 224 is also provided with localizing sensors 237 to position the localizing sensors 237 on the tibia of the knee. The localizing sensors 236 or 237 could be of any type (electromagnetic, opto-electronic, ultrasonic, retro-reflective, etc.) and could provide data on their three-dimensional positions or their three-dimensional positions and orientations, with respect to an external reference, or with respect to one another. Their positions are tracked using a camera (not shown). When using ultrasonic sensors, their positions are tracked by a ultrasound tx/rx. Their three-dimensional position and orientation can also be determined by their relationship to one another. When using electromagnetic tracking sensors their three-dimensional position and orientation is tracked with an electromagnetic field emitter/receiver.

The harness 200 and the tibial attachment bar 224 are installed on the knee to be analyzed. A knee posture is adopted or movement of the knee is performed. This movement could consist of walking, or walking on a treadmill, or bending and/or stretching the knee. The movement could be guided by a person or by an apparatus. Data is generated by the localizing sensors 236 and 237, and the data is treated and analyzed by computerized program means 238 or equivalent electronic means. The treatment of the data could reside in the calculation of mathematical relationships relating the femur to the tibia in space using initially the above-described calibration methods. These relationships could be calculated with the definition on the femur and on the tibia of a coordinate system representing the location of the femur and the tibia, respectively. This latter definition could be accomplished on computerized models which are thereafter calibrated on real bones.

The mathematical relationships, rotations, translations, helicoidal axis, etc., are used to calculate knee movement indexes data 239 used in the description of the posture, or the movement of the knee.

Briefly summarizing the method of determining the kinematic of a knee in a non-evasive manner comprising the harness of the present invention, the method comprises attaching the harness about a knee femur in the manner as above described and securing the tibial attachment rod to the knee tibia in a fixed relationship. Data is generated by the localizing sensors secured to the harness and the tibial attachment rod. This data localizes the sensors in space and in time. The location of the sensors is detected at specific time intervals to provide location data at the time intervals. This data is treated, analyzed and resulting data is generated which describes the knee to which the harness and tibial attachment means is secured.

In installing the harness about the knee care is taken to place one of the clamping means between the vastus medialis and the sartorius tendon of the knee. The other clamping means is positioned between the ilio-tibial band and the biceps femoris tendon of the knee. The attachment rod which is connected to the harness is placed against the medial side of thigh and attached by means of straps above the knee. The stability of the harness is verified even after the knee has been flexed a few times. The position of the stabilizing element on the medial side is adjusted so that one extremity urges against the skin in alignment with the center of the condyle when the knee is in extension. The position of the attachment means is adjusted so that it urges on the interior side of the tibia below the two tuberosity of the tibia and it is attached below the two tuberosity of the tibia.

The measurements are taken when the knee is in movement and this is achieved by walking on a floor surface or walking on a treadmill or jumping at least one or a few times, or bending the knee at least once or stretching the knee at least one time. The movement is guided by a person or an apparatus.

Figure 14:
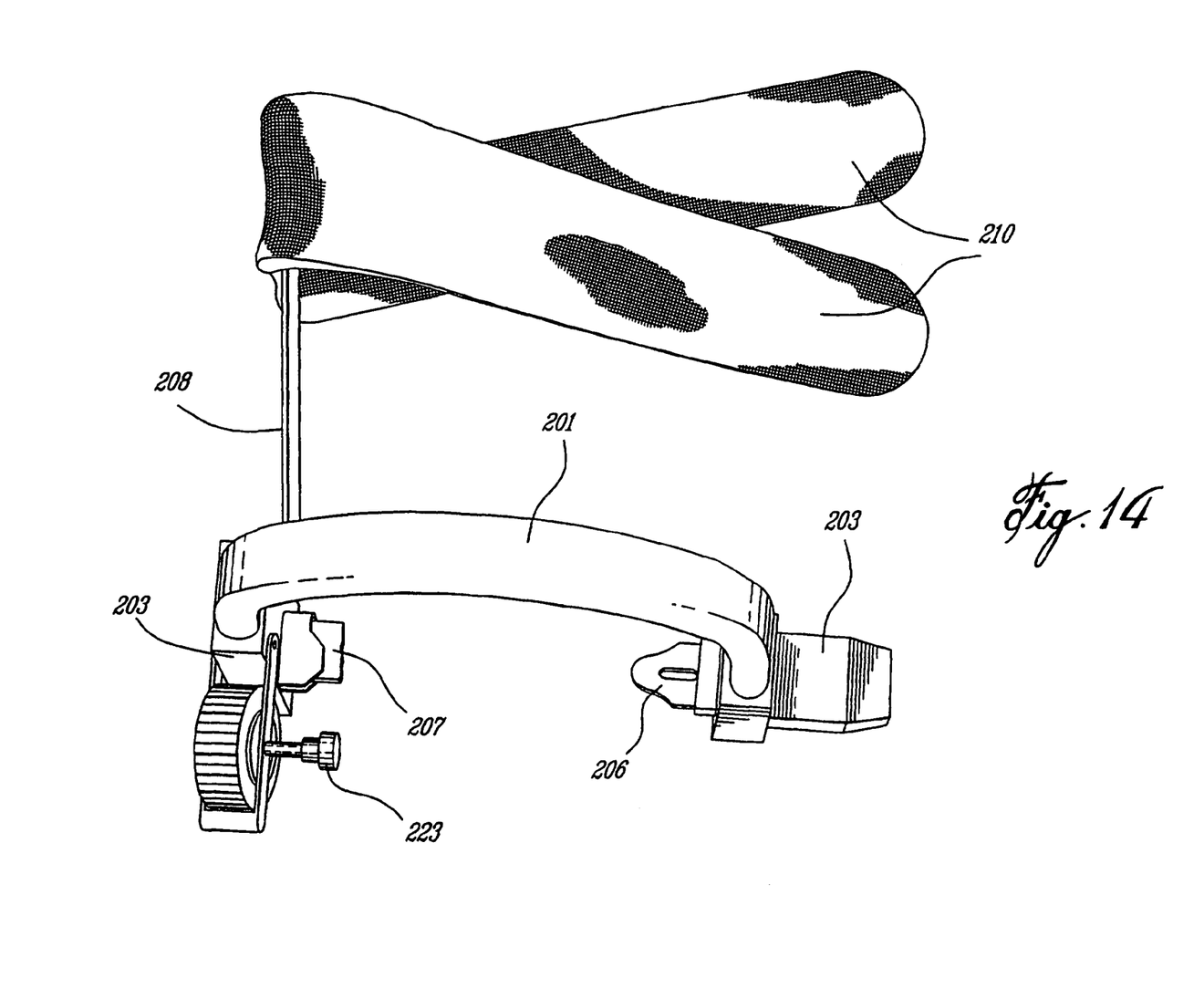
FIG. 14 is a perspective view of the harness as assembled for being used on a left leg.

FIGS. 12 to 15 show the various elements of the harness 200 as disassembled and mounted for being used either on the right femur (FIG. 12) or the left knee (FIG. 14). It is pointed out that the medial rigid support 203 is reduced in width so as to prevent it from impeding the gait of the patient. It has also been thought to use two harnesses at the same time, for either leg.

It is within the ambit of the present invention to cover any obvious modifications of the embodiments described herein, provided such modifications fall within the scope of the appended claims.

The invention claimed is:

1. A method for creating a frame of reference of a leg of a subject for subsequent 3-D kinematic analysis of the leg with non-invasive trackable references secured to the femur and the tibia of the leg, comprising the steps of:
   i) obtaining tibial and femoral axes with respect to the trackable references by tracking points and motions of the leg, the femoral axis intersecting a femoral head center and a knee reference point, and the tibial axis intersecting said knee reference point and a tibial reference point;
   ii) registering a known posture of the subject with respect to the trackable references, the known posture having the subject standing against a wall with the feet in a known position, such that a frontal plane of the subject is parallel to the wall and a sagittal plane of the subject incorporates a normal to the frontal plane and a vector intersecting the femoral head center and the tibial reference point;
   iii) obtaining a desired posture of the subject with respect to the trackable references as a function of the known posture by tracking a predetermined motion of the leg, said predetermined motion of the leg including flexion/extension motions, the desired posture being obtained at a full extension with respect to said tibial and femoral axes, such that the frame of reference includes a tibial coordinate system originating from the knee reference point and having said tibial axis, a second tibial axis perpendicular to said tibial axis and lying in the sagittal plane and a third tibial axis perpendicular to said tibial axis and the second tibial axis, and a femoral coordinate system originating from the knee reference point and having said femoral axis, a second femoral axis perpendicular to said femoral axis and lying in the sagittal plane and a third femoral axis perpendicular to said femoral axis and the second femoral axis;
   iv) setting a frame of reference to said tibial and femoral axis of the leg in the desired posture of the subject with respect to the trackable references;
   v) tracking movement of the leg with respect to the frame of reference of the leg; and
   vi) performing a 3-D kinematic analysis of the leg using said movement of the leg to establish a diagnosis.

2. The method according to claim 1, wherein the feet in the known position are positioned in a template.

3. The method according to claim 1, wherein the known position of the feet includes the foot of the referenced leg being position in elevation such that a predetermined angle between said femoral axis and tibial axis is obtained.

* * * * *